(12) United States Patent
Wang et al.

(10) Patent No.: US 11,034,771 B2
(45) Date of Patent: *Jun. 15, 2021

(54) ANTI-CD73 ANTI-PD-L1 BISPECIFIC ANTIBODIES

(71) Applicant: I-Mab Biopharma US Limited, Gaithersburg, MD (US)

(72) Inventors: Zhengyi Wang, Shanghai (CN); Lei Fang, Shanghai (CN); Bingshi Guo, Shanghai (CN); Jingwu Zang, Shanghai (CN); Qiumei Yang, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/963,091

(22) PCT Filed: Jul. 25, 2019

(86) PCT No.: PCT/CN2019/097774
§ 371 (c)(1),
(2) Date: Jul. 17, 2020

(87) PCT Pub. No.: WO2020/020307
PCT Pub. Date: Jan. 30, 2020

(65) Prior Publication Data
US 2020/0347146 A1    Nov. 5, 2020

(30) Foreign Application Priority Data

Jul. 25, 2018 (WO) ................ PCT/CN2018/096949

(51) Int. Cl.
*C07K 16/28* (2006.01)

(52) U.S. Cl.
CPC ...... *C07K 16/2896* (2013.01); *C07K 16/2827* (2013.01); *C07K 2317/31* (2013.01); *C07K 2317/55* (2013.01); *C07K 2317/565* (2013.01); *C07K 2317/569* (2013.01); *C07K 2317/622* (2013.01)

(58) Field of Classification Search
CPC ............. C07K 16/2827; C07K 16/468; C07K 2317/31
See application file for complete search history.

(56) References Cited

U.S. PATENT DOCUMENTS

| | | | |
|---|---|---|---|
| 7,820,161 B1 | 10/2010 | Curd et al. | |
| 8,617,546 B2 | 12/2013 | Kang et al. | |
| 9,388,243 B2 | 7/2016 | Cheong et al. | |
| 10,059,769 B2 | 8/2018 | Fang et al. | |
| 10,208,119 B2 | 2/2019 | Fang et al. | |
| 10,584,169 B2* | 3/2020 | Wang .................... | C07K 16/40 |
| 2009/0203538 A1 | 8/2009 | Sugioka | |
| 2013/0045202 A1 | 2/2013 | Irving et al. | |
| 2013/0122014 A1 | 5/2013 | Korman et al. | |
| 2015/0203580 A1 | 7/2015 | Papadopoulos et al. | |
| 2016/0194407 A1 | 7/2016 | Hay et al. | |
| 2016/0272712 A1 | 9/2016 | Freeman et al. | |
| 2017/0058033 A1 | 3/2017 | Ludwig et al. | |
| 2017/0306025 A1 | 10/2017 | Du et al. | |
| 2018/0346571 A1 | 12/2018 | Gurney et al. | |
| 2019/0083644 A1 | 3/2019 | Yoo et al. | |
| 2020/0157222 A1* | 5/2020 | Fang ................ | A61P 35/00 |

FOREIGN PATENT DOCUMENTS

| | | |
|---|---|---|
| CN | 1378459 A1 | 11/2002 |
| CN | 104211814 A1 | 12/2014 |
| CN | 105461808 A | 4/2016 |
| CN | 107488229 A | 12/2017 |
| WO | 20070005874 A1 | 1/2007 |
| WO | 20100077634 A1 | 7/2010 |
| WO | 20130079174 A1 | 6/2013 |
| WO | 2014100079 A1 | 6/2014 |
| WO | 2016024228 A1 | 2/2016 |
| WO | 2016055609 A1 | 4/2016 |
| WO | 2016061142 A1 | 4/2016 |
| WO | 2016075099 A1 | 5/2016 |
| WO | 2016075176 A1 | 5/2016 |
| WO | 2016081746 A1 | 5/2016 |
| WO | WO 2016/081748 | 5/2016 |
| WO | 2016131950 A1 | 8/2016 |
| WO | 2017097407 A1 | 6/2017 |
| WO | WO 2017/218435 | 12/2017 |
| WO | WO 2017/220989 | 12/2017 |
| WO | WO 2017/220990 | 12/2017 |
| WO | WO 2018/137598 | 8/2018 |

OTHER PUBLICATIONS

International Search Report and Written Opinion for PCT/CN2019/097774 dated Oct. 30, 2019, 13 pages.
Sanchez-Paulete et al., "Cancer Immunotherapy with immunomodulatory anti-CD137 and anti-PD-1 monoclonal antibodies requires Batf3-dependent dendritic cells", Cancer Discov., vol. 6, No. 1, pp. 71-79, 2016.
Lai et al., "CD4+ T Cell-Derived IL-2 Signals During Early Advances Primary CD8+ T Cell Responses", PLoS ONE, 4(11): e7766, Nov. 10, 2009, 14 pages.
Abdiche et al., Assessing Kinetic and Epitopic Diversity Across Orthogonal Monoclonal Antibody Generation Platforms, mAbs, 2016, 8:264-277.
Boyd et al., Deep Sequencing and Human Antibody repertoire Analysis, Current Opinion in immunology 2016 40: 103-109.
Boyerinas et al., Antibody-Dependent Cellular Cytotoxicity Activity of a Novel Anti-PD-L1 Antibody Avelumab (MSB0010718C) on Human Tumor Cells, Cancer Immunology Research, vol. 3, No. 10, May 26, 2015, pp. 1148-1157.

(Continued)

*Primary Examiner* — Jessica H Roark
(74) *Attorney, Agent, or Firm* — Sheppard Mullin Richter & Hampton LLP

(57) ABSTRACT

Provided are bispecific antibodies capable of binding to human CD73 protein and human PD-L1 protein. These bispecific antibodies are effective in treating cancer.

23 Claims, 8 Drawing Sheets

Specification includes a Sequence Listing.

(56) References Cited

OTHER PUBLICATIONS

Conroy et al., Antibodies: From Novel Repertoires to Defining and Refining the Structure of Biologically Important Targets, Methods, 2017, 116: 12-22.

Ferrara et al., Recombinant Renewable Polyclonal Antibodies, mAbs, 5 7: 32-41, (2014).

Ishida et al.; Differential expression of PD-L1 and PD-L2, ligands for an inhibitory receptor PD-1, in the cells of lymphohematopoietic tissues, Immunol Lett. 2002; 84: pp. 57-62.

Khan et al., Cross-neutralizing Anti-HIV-1 Human Single Chain Variable Fragments (scFvs) Against CD4 Binding Site and N332 Glycan Identified from a Recombinant Phage Library, Sci. Rep., 2017, 7, 45163, doi: 10.1038/srep45163, 12 pages.

Könitzer et al., Generation of Highly Diverse Panel of Antagonistic Chicken Monoclonal Antibodies Against the GIP Receptor, mAbs, 2017, 9:536-549.

Lee et al., Molecular-level analysis of the serum antibody repertoire in young adults before and after seasonal influenza vaccination, Nature Medicine, 2016, 22:1456-1464.

Li et al., Cloning, prokaryotic expression of human PD-L1 and preparation of its antibody, Med J Chin PLA, vol. 35, No. 8, Aug. 1, 2010, pp. 997-999 (English Abstract).

Parola et al., Integrating High-Throughput Screening and Sequencing for Monoclonal Antibody Discovery and Engineering, Immunology, 2018, 153:31-41.

Sheehan et al., Phage and Yeast Display, Microbiol. Spectr. 2015 3(1): AID-0028-2014, 17 pages.

Sun et al. Preparation and characterization of three novel monoclonal antibodies against human PD-L1, Chinese Doctoral Dissertations & Master's These Full-text Database (Master) Nedicine and Health Sciences, Dec. 15, 2006. E059-242, English Abstract only.

Taube et al., Colocalization of inflammatory response with B7-h1 expression in human melanocytic lesions supports an adaptive resistance mechanism of immune escape, Sci Transl Med. 2012:4(127): 127ra37; p. 1-22.

Van Regenmortel, Development of a Preventive HIV Vaccine Requires Solving Inverse Problems which is Unattainable by Rational Vaccine Design, Front. Immunol., 2018, vol. 8, Article 2009, 11 pages.

Zhou, Preparation and characterization of three novel rnonoclonal antibodies against human PD-L1, Chinese Master's Theses Full-text Database Medicine and Health Sciences, Jun. 15, 2012 (English Abstract).

European Search Report for EP 18733153.3 dated Aug. 9, 2019 (11 pages).

Geoghegan et al., "Inhibition of CD73 AMP hydrolysis by a therapeutic antibody with a dual, non-competitive mechanism of action", MABS, vol. 8, No. 3, pp. 454-467, 2016.

\* cited by examiner

SEQUENCE LISTING

```
<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Ser Gly Tyr Tyr Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Tyr Ile Asn Tyr Gly Gly Ser Asn Gly Tyr Asn Pro Ser Leu Lys Ser
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Asp Tyr Asp Ala Tyr Tyr Glu Ala Leu Asp Asp
1               5                   10

<210> SEQ ID NO 4
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 4

Arg Ala Ser Ser Arg Val Asn Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Trp Ser Ser Asn Pro Pro Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Ser Tyr Asp Met Ser
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Thr Ile Ser Asp Ala Gly Gly Tyr Ile Tyr Tyr Arg Asp Ser Val Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Glu Leu Pro Trp Arg Tyr Ala Leu Asp Tyr
1               5                   10

<210> SEQ ID NO 10
<211> LENGTH: 11
<212> TYPE: PRT
<213> ORGANISM: Artificial Sequence
```

```
<220> FEATURE:
<223> OTHER INFORMATION: Synthetic

<400> SEQUENCE: 10

Lys Ala Ser Gln Asp Val Thr Pro Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Ser Thr Ser Ser Arg Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Gln Gln His Tyr Thr Thr Pro Leu Thr
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Gly Gly Gly Gly Ser Gly Gly Gly Ser Gly Gly Gly Gly Ser
1               5                   10                  15

<210> SEQ ID NO 14
<211> LENGTH: 64
<212> TYPE: PRT
<213> ORGANISM: Artificial Sequence
<220> FEATURE:
<223> OTHER INFORMATION: Synthetic

<400> SEQUENCE: 14

Pro Cys Glu Pro Thr Lys Thr Glu Arg Glu Gln Glu Lys Glu
1               5                   10                  15

Lys Glu Lys Lys Lys Glu Glu Gly Gly Arg Gly Thr Asn Arg Thr Thr
            20                  25                  30

Ala Pro Ala Thr Thr Ala Lys Ala Leu Ser Gly Glu Ala Gln Pro Gln
        35                  40                  45

Ala Thr Pro Val Ser Ser Ala Gln Ala Lys Pro Ser Glu Pro Trp Arg
    50                  55                  60

<210> SEQ ID NO 15
<211> LENGTH: 706
<212> TYPE: PRT
<213> ORGANISM: Artificial Sequence
<220> FEATURE:
<223> OTHER INFORMATION: Synthetic

<400> SEQUENCE: 15
```

```
Glu Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Thr Ser Gly
             20                  25                  30

Tyr Tyr Trp Asn Trp Ile Arg Gln Pro Pro Gly Lys Lys Leu Glu Trp
         35                  40                  45

Met Gly Tyr Ile Asn Tyr Gly Ser Asn Gly Tyr Asn Pro Ser Leu
 50                  55                  60

Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
             85                  90                  95

Ala Arg Asp Tyr Asp Ala Tyr Tyr Glu Ala Leu Asp Asp Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                420               425                430
Glu Ala Leu His Asn His Tyr Thr Gln Lys Ser Leu Ser Leu Ser Pro
        435                 440                 445
Gly Lys Gly Gly Gly Ser Gly Gly Gly Ser Gly Gly Gly Gly
    450                 455                 460
Ser Glu Val Gln Leu Val Glu Ser Gly Gly Leu Val Gln Pro Gly
465                 470                 475                 480
Gly Ser Leu Arg Leu Ser Cys Ala Ala Ser Gly Phe Thr Phe Ser Ser
                485                 490                 495
Tyr Asp Met Ser Trp Val Arg Gln Ala Pro Gly Lys Ser Leu Glu Trp
            500                 505                 510
Val Ala Thr Ile Ser Asp Ala Gly Gly Tyr Ile Tyr Tyr Arg Asp Ser
            515                 520                 525
Val Lys Gly Arg Phe Thr Ile Ser Arg Asp Asn Ala Lys Asn Ser Leu
    530                 535                 540
Tyr Leu Gln Met Asn Ser Leu Arg Asp Glu Asp Thr Ala Val Tyr Ile
545                 550                 555                 560
Cys Ala Arg Glu Leu Pro Trp Arg Tyr Ala Leu Asp Tyr Trp Gly Gln
                565                 570                 575
Gly Thr Thr Val Thr Val Ser Ser Gly Gly Gly Ser Gly Gly Gly
            580                 585                 590
Gly Ser Gly Gly Gly Gly Ser Asp Ile Gln Met Thr Gln Ser Pro Ser
        595                 600                 605
Ser Leu Ser Ala Ser Val Gly Asp Arg Val Thr Ile Thr Cys Lys Ala
    610                 615                 620
Ser Gln Asp Val Thr Pro Ala Val Ala Trp Tyr Gln Gln Lys Pro Gly
625                 630                 635                 640
Lys Ala Pro Lys Leu Leu Ile Tyr Ser Thr Ser Ser Arg Tyr Thr Gly
                645                 650                 655
Val Pro Ser Arg Phe Ser Gly Ser Gly Ser Gly Thr Asp Phe Thr Phe
            660                 665                 670
Thr Ile Ser Ser Leu Gln Pro Glu Asp Ile Ala Thr Tyr Tyr Cys Gln
        675                 680                 685
Gln His Tyr Thr Thr Pro Leu Thr Phe Gly Gln Gly Thr Lys Leu Glu
    690                 695                 700
Ile Lys
705

<210> SEQ ID NO 16
<211> LENGTH: 213
<212> TYPE: PRT
<213> ORGANISM: Artificial Sequence
<220> FEATURE:
<223> OTHER INFORMATION: Synthetic

<400> SEQUENCE: 16

Glu Ile Val Leu Ser Gln Ser Pro Ala Thr Leu Ser Leu Ser Pro Gly
1               5                   10                  15
Glu Arg Ala Thr Leu Ser Cys Arg Ala Ser Ser Arg Val Asn Tyr Met
            20                  25                  30
His Trp Tyr Gln Gln Lys Pro Gly Gln Ser Pro Arg Pro Trp Ile Ser
        35                  40                  45
Ala Thr Ser Asn Leu Ala Ser Gly Val Pro Ala Arg Phe Ser Gly Ser
    50                  55                  60
Gly Ser Gly Thr Ser Tyr Thr Leu Thr Ile Ser Ser Leu Glu Pro Glu
```

```
                65                  70                  75                  80
Asp Phe Ala Val Tyr Tyr Cys Gln Gln Trp Ser Ser Asn Pro Pro Thr
                    85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 17
<211> LENGTH: 755
<212> TYPE: PRT
<213> ORGANISM: Artificial Sequence
<220> FEATURE:
<223> OTHER INFORMATION: Synthetic

<400> SEQUENCE: 17

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
                20                  25                  30

Tyr Tyr Trp Asn Trp Ile Arg Gln Pro Pro Gly Lys Lys Leu Glu Trp
            35                  40                  45

Met Gly Tyr Ile Asn Tyr Gly Gly Ser Asn Tyr Asn Pro Ser Leu
50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Tyr Asp Ala Tyr Tyr Glu Ala Leu Asp Asp Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
```

```
              210                 215                 220
Lys Thr His Thr Cys Pro Pro Cys Pro Ala Pro Glu Leu Leu Gly Gly
225                 230                 235                 240

Pro Ser Val Phe Leu Phe Pro Lys Pro Lys Asp Thr Leu Met Ile
                245                 250                 255

Ser Arg Thr Pro Glu Val Thr Cys Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys Pro Cys Glu Pro Thr Lys Thr Glu Arg Glu Glu Gln Glu Glu
        450                 455                 460

Lys Glu Lys Glu Lys Lys Glu Glu Gly Gly Arg Gly Thr Asn Arg
465                 470                 475                 480

Thr Thr Ala Pro Ala Thr Ala Lys Ala Leu Ser Gly Glu Ala Gln
                485                 490                 495

Pro Gln Ala Thr Pro Val Ser Ala Gln Ala Lys Pro Ser Glu Pro
                500                 505                 510

Trp Arg Glu Val Gln Leu Val Glu Ser Gly Gly Leu Val Gln Pro
                515                 520                 525

Gly Gly Ser Leu Arg Leu Ser Cys Ala Ala Ser Gly Phe Thr Phe Ser
        530                 535                 540

Ser Tyr Asp Met Ser Trp Val Arg Gln Ala Pro Gly Lys Ser Leu Glu
545                 550                 555                 560

Trp Val Ala Thr Ile Ser Asp Ala Gly Gly Tyr Ile Tyr Tyr Arg Asp
                565                 570                 575

Ser Val Lys Gly Arg Phe Thr Ile Ser Arg Asp Asn Ala Lys Asn Ser
                580                 585                 590

Leu Tyr Leu Gln Met Asn Ser Leu Arg Asp Glu Asp Thr Ala Val Tyr
                595                 600                 605

Ile Cys Ala Arg Glu Leu Pro Trp Arg Tyr Ala Leu Asp Tyr Trp Gly
                610                 615                 620

Gln Gly Thr Thr Val Thr Val Ser Ser Gly Gly Gly Gly Ser Gly Gly
625                 630                 635                 640
```

```
Gly Gly Ser Gly Gly Gly Ser Asp Ile Gln Met Thr Gln Ser Pro
                645                 650                 655

Ser Ser Leu Ser Ala Ser Val Gly Asp Arg Val Thr Ile Thr Cys Lys
            660                 665                 670

Ala Ser Gln Asp Val Thr Pro Ala Val Ala Trp Tyr Gln Gln Lys Pro
        675                 680                 685

Gly Lys Ala Pro Lys Leu Leu Ile Tyr Ser Thr Ser Ser Arg Tyr Thr
    690                 695                 700

Gly Val Pro Ser Arg Phe Ser Gly Ser Gly Ser Gly Thr Asp Phe Thr
705                 710                 715                 720

Phe Thr Ile Ser Ser Leu Gln Pro Glu Asp Ile Ala Thr Tyr Tyr Cys
                725                 730                 735

Gln Gln His Tyr Thr Thr Pro Leu Thr Phe Gly Gln Gly Thr Lys Leu
            740                 745                 750

Glu Ile Lys
        755

<210> SEQ ID NO 18
<211> LENGTH: 705
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Ser Leu Glu Trp Val
        35                  40                  45

Ala Thr Ile Ser Asp Ala Gly Gly Tyr Ile Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Ile Cys
                85                  90                  95

Ala Arg Glu Leu Pro Trp Arg Tyr Ala Leu Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
        290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys Gly Gly Gly Gly Ser Gly Gly Gly Ser Gly Gly Gly Gly Ser
            450             455             460

Glu Val Gln Leu Gln Glu Ser Gly Pro Gly Leu Val Lys Pro Ser Glu
465             470             475             480

Thr Leu Ser Leu Thr Cys Ala Val Ser Gly Tyr Ser Ile Thr Ser Gly
                485             490             495

Tyr Tyr Trp Asn Trp Ile Arg Gln Pro Pro Gly Lys Lys Leu Glu Trp
            500             505             510

Met Gly Tyr Ile Asn Tyr Gly Gly Ser Asn Gly Tyr Asn Pro Ser Leu
            515             520             525

Lys Ser Arg Ile Thr Ile Ser Arg Asp Thr Ser Lys Asn Gln Phe Ser
            530             535             540

Leu Lys Leu Ser Ser Val Thr Ala Ala Asp Thr Ala Val Tyr Tyr Cys
545             550             555             560

Ala Arg Asp Tyr Asp Ala Tyr Tyr Glu Ala Leu Asp Asp Trp Gly Gln
            565             570             575

Gly Thr Thr Val Thr Val Ser Ser Gly Gly Gly Gly Ser Gly Gly Gly
            580             585             590

Gly Ser Gly Gly Gly Gly Ser Glu Ile Val Leu Ser Gln Ser Pro Ala
        595             600             605

Thr Leu Ser Leu Ser Pro Gly Glu Arg Ala Thr Leu Ser Cys Arg Ala
            610             615             620

Ser Ser Arg Val Asn Tyr Met His Trp Tyr Gln Gln Lys Pro Gly Gln
625             630             635             640

Ser Pro Arg Pro Trp Ile Ser Ala Thr Ser Asn Leu Ala Ser Gly Val
            645             650             655
```

```
Pro Ala Arg Phe Ser Gly Ser Gly Ser Gly Thr Ser Tyr Thr Leu Thr
            660                 665                 670

Ile Ser Ser Leu Glu Pro Glu Asp Phe Ala Val Tyr Tyr Cys Gln Gln
        675                 680                 685

Trp Ser Ser Asn Pro Pro Thr Phe Gly Gly Gly Thr Lys Val Glu Ile
    690                 695                 700

Lys
705

<210> SEQ ID NO 19
<211> LENGTH: 214
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 754
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Asp Met Ser Trp Val Arg Gln Ala Pro Gly Lys Ser Leu Glu Trp Val
         35                  40                  45

Ala Thr Ile Ser Asp Ala Gly Gly Tyr Ile Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu Pro Trp Arg Tyr Ala Leu Asp Tyr Trp Gly Gln Gly
             100                 105                 110

Thr Thr Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
     210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
     290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Glu Glu Met Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro Gly
         435                 440                 445
```

Lys Pro Cys Glu Pro Thr Lys Thr Glu Arg Glu Glu Gln Glu Glu Lys
            450                 455                 460

Glu Lys Glu Lys Lys Glu Glu Gly Gly Arg Gly Thr Asn Arg Thr
465                 470                 475                 480

Thr Ala Pro Ala Thr Thr Ala Lys Ala Leu Ser Gly Glu Ala Gln Pro
                485                 490                 495

Gln Ala Thr Pro Val Ser Ser Ala Gln Ala Lys Pro Ser Glu Pro Trp
            500                 505                 510

Arg Glu Val Gln Leu Gln Glu Ser Gly Pro Gly Leu Val Lys Pro Ser
            515                 520                 525

Glu Thr Leu Ser Leu Thr Cys Ala Val Ser Gly Tyr Ser Ile Thr Ser
530                 535                 540

Gly Tyr Tyr Trp Asn Trp Ile Arg Gln Pro Pro Gly Lys Lys Leu Glu
545                 550                 555                 560

Trp Met Gly Tyr Ile Asn Tyr Gly Gly Ser Asn Gly Tyr Asn Pro Ser
                565                 570                 575

Leu Lys Ser Arg Ile Thr Ile Ser Arg Asp Thr Ser Lys Asn Gln Phe
            580                 585                 590

Ser Leu Lys Leu Ser Ser Val Thr Ala Ala Asp Thr Ala Val Tyr Tyr
            595                 600                 605

Cys Ala Arg Asp Tyr Asp Ala Tyr Tyr Glu Ala Leu Asp Asp Trp Gly
            610                 615                 620

Gln Gly Thr Thr Val Thr Val Ser Ser Gly Gly Gly Ser Gly Gly
625                 630                 635                 640

Gly Gly Ser Gly Gly Gly Ser Glu Ile Val Leu Ser Gln Ser Pro
                645                 650                 655

Ala Thr Leu Ser Leu Ser Pro Gly Glu Arg Ala Thr Leu Ser Cys Arg
            660                 665                 670

Ala Ser Ser Arg Val Asn Tyr Met His Trp Tyr Gln Gln Lys Pro Gly
            675                 680                 685

Gln Ser Pro Arg Pro Trp Ile Ser Ala Thr Ser Asn Leu Ala Ser Gly
            690                 695                 700

Val Pro Ala Arg Phe Ser Gly Ser Gly Ser Gly Thr Ser Tyr Thr Leu
705                 710                 715                 720

Thr Ile Ser Ser Leu Glu Pro Glu Asp Phe Ala Val Tyr Tyr Cys Gln
                725                 730                 735

Gln Trp Ser Ser Asn Pro Pro Thr Phe Gly Gly Gly Thr Lys Val Glu
            740                 745                 750

Ile Lys

<210> SEQ ID NO 21
<211> LENGTH: 120
<212> TYPE: PRT
<213> ORGANISM: Artificial Sequence
<220> FEATURE:
<223> OTHER INFORMATION: Synthetic

<400> SEQUENCE: 21

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Tyr Trp Asn Trp Ile Arg Gln Pro Pro Gly Lys Lys Leu Glu Trp
        35                  40                  45

Met Gly Tyr Ile Asn Tyr Gly Gly Ser Asn Gly Tyr Asn Pro Ser Leu

```
            50                  55                  60
Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                     85                  90                  95

Ala Arg Asp Tyr Asp Ala Tyr Tyr Glu Ala Leu Asp Asp Trp Gly Gln
                100                 105                 110

Gly Thr Thr Val Thr Val Ser Ser
            115                 120
```

<210> SEQ ID NO 22
<211> LENGTH: 106
<212> TYPE: PRT
<213> ORGANISM: Artificial Sequence
<220> FEATURE:
<223> OTHER INFORMATION: Synthetic

<400> SEQUENCE: 22

```
Glu Ile Val Leu Ser Gln Ser Pro Ala Thr Leu Ser Leu Ser Pro Gly
  1               5                  10                  15

Glu Arg Ala Thr Leu Ser Cys Arg Ala Ser Ser Arg Val Asn Tyr Met
                 20                  25                  30

His Trp Tyr Gln Gln Lys Pro Gly Gln Ser Pro Arg Pro Trp Ile Ser
             35                  40                  45

Ala Thr Ser Asn Leu Ala Ser Gly Val Pro Ala Arg Phe Ser Gly Ser
         50                  55                  60

Gly Ser Gly Thr Ser Tyr Thr Leu Thr Ile Ser Ser Leu Glu Pro Glu
 65                  70                  75                  80

Asp Phe Ala Val Tyr Tyr Cys Gln Gln Trp Ser Ser Asn Pro Pro Thr
                 85                  90                  95

Phe Gly Gly Gly Thr Lys Val Glu Ile Lys
            100                 105
```

<210> SEQ ID NO 23
<211> LENGTH: 119
<212> TYPE: PRT
<213> ORGANISM: Artificial Sequence
<220> FEATURE:
<223> OTHER INFORMATION: Synthetic

<400> SEQUENCE: 23

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Ser Leu Glu Trp Val
             35                  40                  45

Ala Thr Ile Ser Asp Ala Gly Gly Tyr Ile Tyr Tyr Arg Asp Ser Val
         50                  55                  60

Lys Gly Arg Phe Thr Ile Ser Arg Asp Asn Lys Asn Ser Leu Tyr
 65                  70                  75                  80

Leu Gln Met Asn Ser Leu Arg Asp Glu Asp Thr Ala Val Tyr Ile Cys
                 85                  90                  95

Ala Arg Glu Leu Pro Trp Arg Tyr Ala Leu Asp Tyr Trp Gly Gln Gly
            100                 105                 110

Thr Thr Val Thr Val Ser Ser
            115
```

```
<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Pro Ala
            20                  25                  30

Val Ala Trp Tyr Gln Gln Lys Pro Gly Lys Ala Pro Lys Leu Leu Ile
        35                  40                  45

Tyr Ser Thr Ser Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Thr Thr Pro Leu
                85                  90                  95

Thr Phe Gly Gln Gly Thr Lys Leu Glu Ile Lys
            100                 105
```

ANTI-CD73 ANTI-PD-L1 BISPECIFIC ANTIBODIES

This application is a U.S. National Stage Application under 35 U.S.C. 371 of International Application No. PCT/CN2019/097774, filed Jul. 25, 2019, which claims priority to International Application PCT/CN2018/096949, filed Jul. 25, 2018. The contents of each of the aforementioned are hereby incorporated by reference in their entirety into the present disclosure.

SEQUENCE LISTING

The instant application contains a Sequence Listing which has been filed electronically in ASCII format and is hereby incorporated by reference in its entirety. Said ASCII copy, created on Jun. 18, 2020, is named 267784US_SL.txt and is 36,782 bytes in size.

BACKGROUND

CD73, cluster of differentiation 73, is also known as 5'-nucleotidase (5'-NT) or ecto-5'-nucleotidase, is an enzyme serves to convert AMP to adenosine. CD73 catalyzes the formation of extracellular adenosine which contributes to the immunosuppressive tumor environment. CD73 is over-expressed in stromal cells and multiple types of tumor cells, as well as in Tregs, M2 Mφs and myeloid derived suppressor cells (MDSCs).

Programmed death-ligand 1 (PD-L1), also known as cluster of differentiation 274 (CD274) or B7 homolog 1 (B7-H1), is a 40 kDa type 1 transmembrane protein believed to play a major role in suppressing the immune system during particular events such as pregnancy, tissue allografts, autoimmune disease and other disease states such as hepatitis. The binding of PD-L1 to PD-1 or B7.1 transmits an inhibitory signal which reduces the proliferation of CD8+ T cells at the lymph nodes and supplementary to that PD-1 is also able to control the accumulation of foreign antigen specific T cells in the lymph nodes through apoptosis which is further mediated by a lower regulation of the gene Bcl-2.

Preclinical evidence shows that CD73 inhibition prevented adenosine-mediated lymphocyte suppression, increased the activity of CD8+ effector cells, and reduced both MDSCs and Tregs. It has been shown that upregulation of PD-L1 may allow cancers to evade the host immune system. An analysis of tumor specimens from patients with renal cell carcinoma found that high tumor expression of PD-L1 was associated with increased tumor aggressiveness and an increased risk of death. Many PD-L1 inhibitors are in development as immuno-oncology therapies and are showing good results in clinical trials.

Bispecific antibodies targeting both the CD73 and PD-L1 proteins have been proposed, but development of bispecific antibodies with good stability and activity has been proved to be challenging.

SUMMARY

The present disclosure provides bispecific antibodies having binding specificities to both CD73 and PD-L1 proteins. As shown in the experimental examples, these bispecific antibodies exhibited high binding affinity to both proteins and were effective in inhibiting CD73 enzymatic activities and blocking PD-L1 to PD-1 binding, resulting in T-cell activation.

DETAILED DESCRIPTION

Definitions

Figure 1:
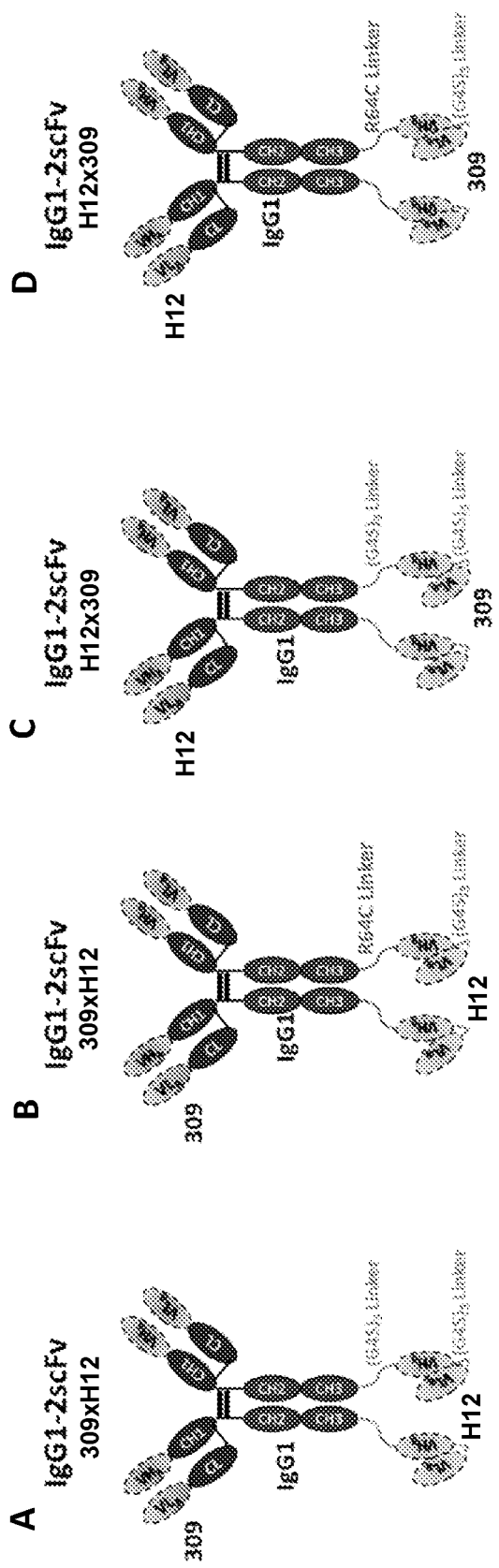
FIG. 1 illustrates the structures of four different bispecific antibodies prepared.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Anti-CD73 Anti-PD-L1 Bispecific Antibodies

The present disclosure provides anti-CD73 anti-PD-L1 bispecific antibodies with high affinity and inhibitory activity to both human CD73 and PD-L1 proteins. The antibodies can bind effectively to both soluble and cell surfaces CD73 and PD-L1. Such bindings were capable of blocking CD73 enzymatic activities and blocking PD-L1 binding to PD-1, resulting in TCR activation and increased IL-2 production.

In accordance with one embodiment of the present disclosure, provided is a bispecific antibody that has binding specificities to both human CD73 and PD-L1 protein. In one embodiment, the bispecific antibody has an anti-CD73 portion that includes CDR regions as shown in Table 1.

TABLE 1

Anti-CD73 CDRs

| Name | Sequences | SEQ ID NO: |
| --- | --- | --- |
| VH CDR1 | SGYYWN | 1 |
| VH CDR2 | YINYGGSNGYNPSLKS | 2 |
| VH CDR3 | DYDAYYEALDD | 3 |
| VL CDR1 | RASSRVNYMH | 4 |
| VL CDR2 | ATSNLAS | 5 |
| VL CDR3 | QQWSSNPPT | 6 |

In one embodiment, the bispecific antibody has an anti-PD-L1 portion that includes CDR regions as shown in Table 2.

TABLE 2

Anti-PD-L1 CDRs

| Name | Sequence | SEQ ID NO: |
| --- | --- | --- |
| VH CDR1 | SYDMS | 7 |
| VH CDR2 | TISDAGGYIYYRDSVKG | 8 |
| VH CDR3 | ELPWRYALDY | 9 |
| VL CDR1 | KASQDVTPAVA | 10 |

TABLE 2-continued

Anti-PD-L1 CDRs

| Name | Sequence | SEQ ID NO: |
| --- | --- | --- |
| VL CDR2 | STSSRYT | 11 |
| VL CDR3 | QQHYTTPLT | 12 |

An example of the heavy chain variable region (VH) of the anti-CD73 portion is SEQ ID NO:21. An example of the light chain variable region (VL) of the anti-CD73 portion is SEQ ID NO:22.

An example of the heavy chain variable region (VH) of the anti-PD-L1 portion is SEQ ID NO:23. An example of the light chain variable region (VL) of the anti-PD-L1 portion is SEQ ID NO:24.

Non-limiting examples of the structures of the bispecific antibody are illustrated in FIG. 1. In one example, the bispecific antibody includes a Fab portion linked to a single-chain variable fragment (scFv). As illustrated in FIG. 1, both antigen-binding domains of the Fab portion can target one protein, whereas the scFv has specificity to the other protein.

Other structures are also contemplated. For example, the bispecific antibody can be a heterodimer, including one heavy chain-light chain pair targeting CD73 and the other heavy chain-light chain pair targeting PD-L1. In some embodiments, one of the heavy chain-light chain pairs can be replaced by a scFv, forming a Fab-scFv structure. In some embodiments, one of the heavy chain-light chain pairs can be replaced by a nanobody (also known as single-domain antibody or VHH), forming a Fab-VHH structure. In some embodiments, both chain-light chain pairs can be replaced by other forms of antigen-binding domains, such as scFv and VHH. In some embodiments, the bispecific antibody can be a single chain, such as having two scFv or VHH connected to each other, or a scFv connected to a VHH, without limitation.

In the Fab/scFv examples of FIG. 1, in some embodiments, the Fab fragments have specificity to CD73 and the scFv fragment has specificity to PD-L1. In some embodiments, the Fab fragments have specificity to PD-L1 and the scFv fragment has specificity to CD73.

A peptide linker can be used to connect the Fab portion (or to the Fc if included) and the scFv portion of the bispecific antibody. Likewise, a linker can be used to connect the heavy chain variable region and the light chain variable region within the scFv. Two examples of such peptide linkers are provided in SEQ ID NO:13 and 14.

Example complete sequences of the heavy chains and light chains of the bispecific antibodies are also provided. In one embodiment, the antibody includes two heavy chains each comprising the amino acid sequence of SEQ ID NO:15 and two light chains each comprising the amino acid sequence of SEQ ID NO:16. In one embodiment, the antibody includes two heavy chains each comprising the amino acid sequence of SEQ ID NO:17 and two light chains each comprising the amino acid sequence of SEQ ID NO:16. In one embodiment, the antibody includes two heavy chains each comprising the amino acid sequence of SEQ ID NO:18 and two light chains each comprising the amino acid sequence of SEQ ID NO:19. In one embodiment, the antibody includes two heavy chains each comprising the amino acid sequence of SEQ ID NO:20 and two light chains each comprising the amino acid sequence of SEQ ID NO:19. It will also be understood by one of ordinary skill in the art that antibodies as disclosed herein may be modified such that they vary in amino acid sequence from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-expresses CD73. In some embodiments, at least one of the cancer cells (e.g., stromal cells) in the patient over-expresses PD-L1.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

Cellular therapies, and more specifically chimeric antigen receptor (CAR) T-cell therapies, are also provided in the present disclosure. A suitable T cell can be used, that is put in contact with a bispecific antibody of the present disclosure (or alternatively engineered to express a bispecific antibody of the present disclosure). Upon such contact or engineering, the T cell can then be introduced to a cancer patient in need of a treatment. The cancer patient may have a cancer of any of the types as disclosed herein. The T cell can be, for instance, a tumor-infiltrating T lymphocyte, a CD4+ T cell, a CD8+ T cell, or the combination thereof, without limitation.

In some embodiments, the T cell was isolated from the cancer patient him- or her-self. In some embodiments, the T cell was provided by a donor or from a cell bank. When the T cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc.

In a further embodiment, the compositions of the disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the disclosure are administered in combination with a chemotherapeutic agent. Chemotherapeutic agents that may be administered with the compositions of the disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1. Preparation of CD73/PD-L1 Bispecific Antibodies

This example describes the preparation of four different bispecific antibodies having specificities to both human CD73 and PD-L1 proteins. The activities of one of them were then tested in vitro.

The structures of the four bispecific antibodies are illustrated in FIG. 1. Each of them included an IgG1 Fab fragment, connected through a linker ((G4S)3, SEQ ID NO:13, or R64C, SEQ ID NO:14), to a single-chain variable fragment (scFv). The anti-CD73 regions are referred to as 309 and the anti-PD-L1 regions are referred to as H12. In panels A and B, the bispecific antibodies included 309 in the Fab portion and H12 in the scFv portion. In panels C and D, the bispecific antibodies included H12 in the Fab portion and 309 in the scFv portion.

In panels A and C, the linkers between the Fab and the scFv were the (G4S)3 linker (SEQ ID NO:13), and the scFv used the R64C linker (SEQ ID NO:14) between the heavy chain variable region and the light chain variable region. In panels B and D, the linkers between the Fab and the scFv were the R64C linker (SEQ ID NO:14), and the scFv used the (G4S)3 linker (SEQ ID NO:13) between the heavy chain variable region and the light chain variable region.

The (G4S)3 linker has the following amino acid sequence: GGGGSGGGGSGGGGS (SEQ ID NO:13). The R64C linker has the following amino acid sequence: PCEPTK-TEREEQEEKEKEKKKEEGGRGTNRTTAPAT-TAKALSGEAQPQATPVSSAQA KPSEPWR (SEQ ID NO:14).

The amino acid sequences of the antibodies and fragments are listed in the table below.

TABLE 3

Amino acid sequences

| Name (SEQ ID NO:) | Sequence |
|---|---|
| A-heavy chain (15) | >309 VH<br>EVQLQESGPGLVKPSETLSLTCAVSGYSITSGYYWNWIRQPPGKKLEWMG<br>YINYGGSNGYNPSLKSRITISRDTSKNQFSLKLSSVTAADTAVYYCARDY<br>DAYYEALDDWGQGTTVTVSS<br><br>>IgG1 CH1-CH2-CH3<br>ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK<br><br>>(G4S)₃ linker<br>GGGGSGGGGSGGGGS<br><br>>H12 VH<br>EVQLVESGGGLVQPGGSLRLSCAASGFTFSSYDMSWVRQAPGKSLEWVAT<br>ISDAGGYIYYRDSVKGRFTISRDNAKNSLYLQMNSLRDEDTAVYICAREL<br>PWRYALDYWGQGTTVTVSS<br><br>>(G4S)₃ linker<br>GGGGSGGGGSGGGGS<br><br>>H12 VL<br>DIQMTQSPSSLSASVGDRVTITCKASQDVTPAVAWYQQKPGKAPKLLIYS<br>TSSRYTGVPSRFSGSGSGTDFTFTISSLQPEDIATYYCQQHYTTPLTFGQ<br>GTKLEIK |
| A-light chain (16) | >309 VL<br>EIVLSQSPATLSLSPGERATLSCRASSRVNYMHWYQQKPGQSPRPWISAT<br>SNLASGVPARFSGSGSGTSYTLTISSLEPEDFAVYYCQQWSSNPPTFGGG<br>TKVEIK<br><br>>IgG1 CL<br>RTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTK<br>SFNRGEC |
| B-heavy chain (17) | >309 VH<br>EVQLQESGPGLVKPSETLSLTCAVSGYSITSGYYWNWIRQPPGKKLEWMG<br>YINYGGSNGYNPSLKSRITISRDTSKNQFSLKLSSVTAADTAVYYCARDY<br>DAYYEALDDWGQGTTVTVSS<br><br>>IgG1 CH1-CH2-CH3<br>ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK<br><br>>R64C linker<br>PCEPTKTEREEQEEKEKEKKKEEGGRGTNRTTAPATTAKALSGEAQPQAT<br>PVSSAQAKPSEPWR<br><br>>H12 VH<br>EVQLVESGGGLVQPGGSLRLSCAASGFTFSSYDMSWVRQAPGKSLEWVAT<br>ISDAGGYIYYRDSVKGRFTISRDNAKNSLYLQMNSLRDEDTAVYICAREL<br>PWRYALDYWGQGTTVTVSS<br><br>>(G4S)₃ linker<br>GGGGSGGGGSGGGGS<br><br>>H12 VL<br>DIQMTQSPSSLSASVGDRVTITCKASQDVTPAVAWYQQKPGKAPKLLIYS<br>TSSRYTGVPSRFSGSGSGTDFTFTISSLQPEDIATYYCQQHYTTPLTFGQ<br>GTKLEIK |

TABLE 3-continued

Amino acid sequences

| Name (SEQ ID NO:) | Sequence |
|---|---|
| B-light chain (16) | >309 VL<br>EIVLSQSPATLSLSPGERATLSCRASSRVNYMHWYQQKPGQSPRPWISAT<br>SNLASGVPARFSGSGSGTSYTLTISSLEPEDFAVYYCQQWSSNPPTFGGG<br>TKVEIK<br><br>>IgG1 CL<br>RTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTK<br>SFNRGEC |
| C-heavy chain (18) | >H12 VH<br>EVQLVESGGGLVQPGGSLRLSCAASGFTFSSYDMSWVRQAPGKSLEWVAT<br>ISDAGGYIYYRDSVKGRFTISRDNAKNSLYLQMNSLRDEDTAVYICAREL<br>PWRYALDYWGQGTTVTVSS<br><br>>IgG1 CH1-CH2-CH3<br>ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK<br><br>>(G4S)$_3$ linker<br>GGGGSGGGGSGGGGS<br><br>>309 VH<br>EVQLQESGPGLVKPSETLSLTCAVSGYSITSGYYWNWIRQPPGKKLEWMG<br>YINYGGSNGYNPSLKSRITISRDTSKNQFSLKLSSVTAADTAVYYCARDY<br>DAYYEALDDWGQGTTVTVSS<br><br>>(G4S)$_3$ linker<br>GGGGSGGGGSGGGGS<br><br>>309 VL<br>EIVLSQSPATLSLSPGERATLSCRASSRVNYMHWYQQKPGQSPRPWISAT<br>SNLASGVPARFSGSGSGTSYTLTISSLEPEDFAVYYCQQWSSNPPTFGGG<br>TKVEIK |
| C-light chain (19) | >H12 VL<br>DIQMTQSPSSLSASVGDRVTITCKASQDVTPAVAWYQQKPGKAPKLLIYS<br>TSSRYTGVPSRFSGSGSGTDFTFTISSLQPEDIATYYCQQHYTTPLTFGQ<br>GTKLEIK<br><br>>IgG1 CL<br>RTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTK<br>SFNRGEC |
| D-heavy chain (20) | >H12 VH<br>EVQLVESGGGLVQPGGSLRLSCAASGFTFSSYDMSWVRQAPGKSLEWVAT<br>ISDAGGYIYYRDSVKGRFTISRDNAKNSLYLQMNSLRDEDTAVYICAREL<br>PWRYALDYWGQGTTVTVSS<br><br>>IgG1 CH1-CH2-CH3<br>ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSCDKTHTCPPCPAPELLGGPSVFLEPPKPKDTLMISRTPEVTCVVVDVS<br>HEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRW<br>QQGNVFSCSVMHEALHNHYTQKSLSLSPGK<br><br>>R64C linker<br>PCEPTKTEREEQEEKEKKKEEGGRGTNRTTAPATTAKALSGEAQPQAT<br>PVSSAQAKPSEPWR<br><br>>309 VH<br>EVQLQESGPGLVKPSETLSLTCAVSGYSITSGYYWNWIRQPPGKKLEWMG<br>YINYGGSNGYNPSLKSRITISRDTSKNQFSLKLSSVTAADTAVYYCARDY<br>DAYYEALDDWGQGTTVTVSS |

TABLE 3-continued

Amino acid sequences

| Name (SEQ ID NO:) | Sequence |
|---|---|
| | >(G4S)3 linker<br>GGGGSGGGGSGGGGS<br><br>>309 VL<br>EIVLSQSPATLSLSPGERATLSCRASSRVNYMHWYQQKPGQSPRPWISAT<br>SNLASGVPARFSGSGSGTSYTLTISSLEPEDFAVYYCQQWSSNPPTFGGG<br>TKVEIK |
| D-light chain (19) | >H12 VL<br>DIQMTQSPSSLSASVGDRVTITCKASQDVTPAVAWYQQKPGKAPKLLIYS<br>TSSRYTGVPSRFSGSGSGTDFTFTISSLQPEDIATYYCQQHYTTPLTFGQ<br>GTKLEIK<br><br>>IgG1 CL<br>RTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTK<br>SFNRGEC |
| 309 heavy chain variable region (21) | EVQLQESGPGLVKPSETLSLTCAVSGYSITSGYYWNWIRQPPGKKLEWMG<br>YINYGGSNGYNPSLKSRITISRDTSKNQFSLKLSSVTAADTAVYYCARDY<br>DAYYEALDDWGQGTTVTVSS |
| 309 light chain variable region (22) | EIVLSQSPATLSLSPGERATLSCRASSRVNYMHWYQQKPGQSPRPWISAT<br>SNLASGVPARFSGSGSGTSYTLTISSLEPEDFAVYYCQQWSSNPPTFGGG<br>TKVEIK |
| H12 heavy chain variable region (23) | EVQLVESGGGLVQPGGSLRLSCAASGFTFSSYDMSWVRQAPGKSLEWVAT<br>ISDAGGYIYYRDSVKGRFTISRDNAKNSLYLQMNSLRDEDTAVYICAREL<br>PWRYALDYWGQGTTVTVSS |
| H12 light chain variable region (24) | DIQMTQSPSSLSASVGDRVTITCKASQDVTPAVAWYQQKPGKAPKLLIYS<br>TSSRYTGVPSRFSGSGSGTDFTFTISSLQPEDIATYYCQQHYTTPLTFGQ<br>GTKLEIK |

The antibodies were purified from 200 ml transiently transfected supernatant of the HEK293F cells by Protein A affinity column. The purity of the antibodies were tested with HPLC and SDS-PAGE.

Example 2. ELISA Binding to Human CD73 and PD-L1 Proteins

This example shows the ELISA binding assay results for structure A (FIG. 1) of the anti-CD73/PD-L1 bispecific antibodies. The antibody is also referred simply as 309-H12. The monospecific antibodies, hu309 (monospecific anti-CD73 antibody with the 309 VH and 309 VL) and H12 (PDL1) (monospecific anti-PD-L1 antibody with the H12 VH and H12 VL), were used as control.

Plated were coated with 100 µl of 1 µg/ml human CD73 protein overnight. The samples were blocked with 1% BSA in PBST for 1 hr, washed with PBST 3×. Binding was tested with 100 µl of serial diluted antibodies (309-H12 or hu309) from 1000 pM by 3-fold, RT for 30 min, washed with PBST 3×. Binding with anti-hu Fc HRP was at 1:10000 in PBST, RT for 30 min, wash with PBST 3×. 100 µl of TMB and 100 µl of HCl were then added.

Figure 2:
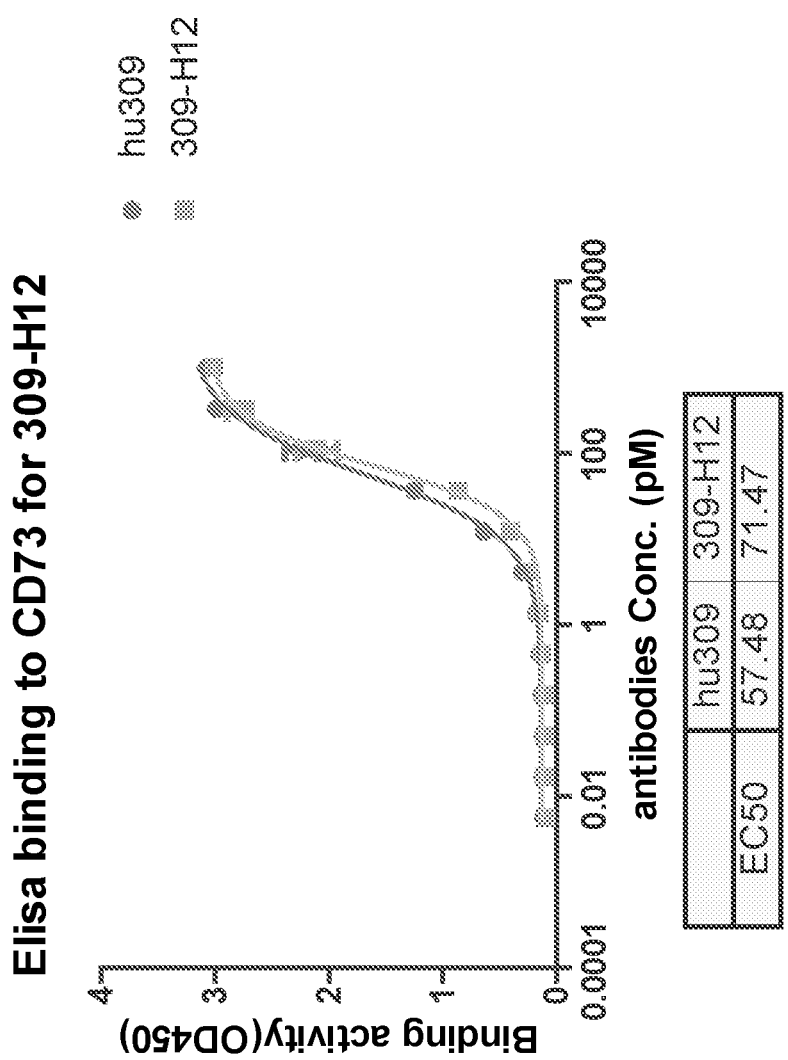
FIG. 2 shows the binding results to soluble CD73 protein.

As shown in FIG. 2, the bispecific antibody 309-H12 had similar binding activities as hu309 in binding to CD73.

Figure 3:
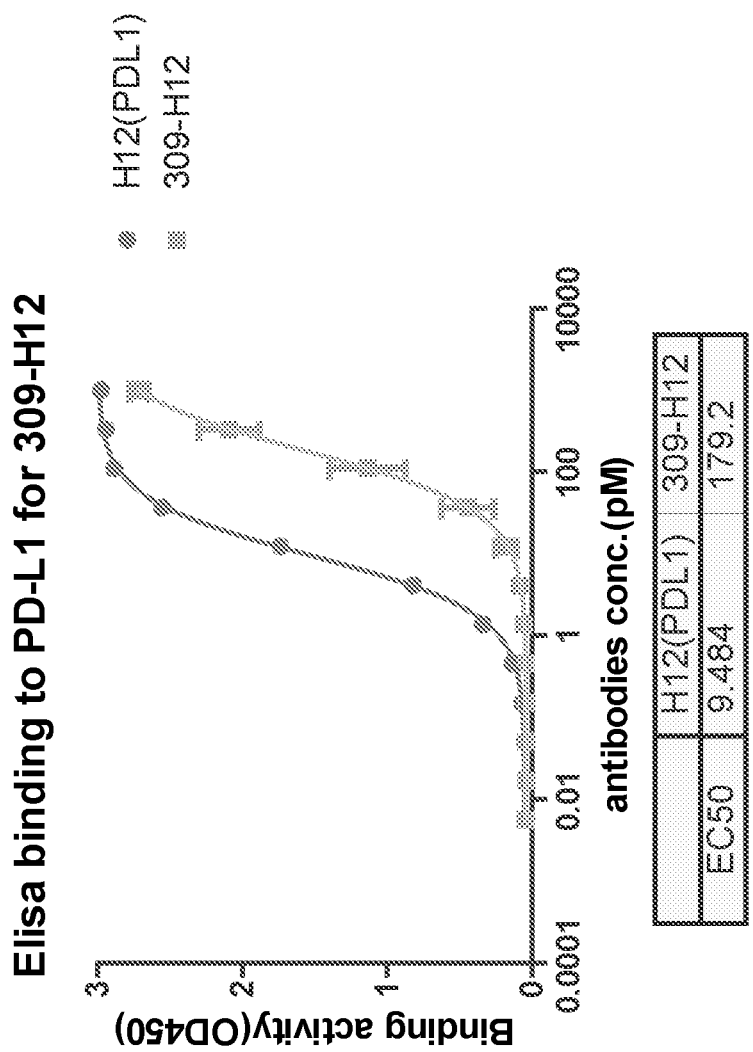
FIG. 3 shows the binding results to soluble PD-L1 protein.

Using the same procedure, the binding activities of 309-H12 and H12(PDL1) to the human PD-L1 protein were tested with ELISA. Although the binding activities of the bispecific antibody was lower than the monospecific one, both of the activities were high (FIG. 3).

Example 3. Cell-Based Binding of the Bispecific Antibody

This example shows the cell-based binding assay results for 309-H12. Like in Example 2, monospecific antibodies hu309 and H12(PDL1) were used as control.

A375 cells that constitutively expressed CD73 on the surface were used in this example. $1 \times 10^5$ A375 cells/well were suspended in FACS buffer. Antibodies diluted from 10 nM by 2-fold, 100 µl into each well, 4° C. for 30 min. The samples were washed with FACS buffer for 1×. AF633-anti hu Fc was added for binding for 30 min at 4° C., and washed with FACS buffer for 1×.

Figure 4:
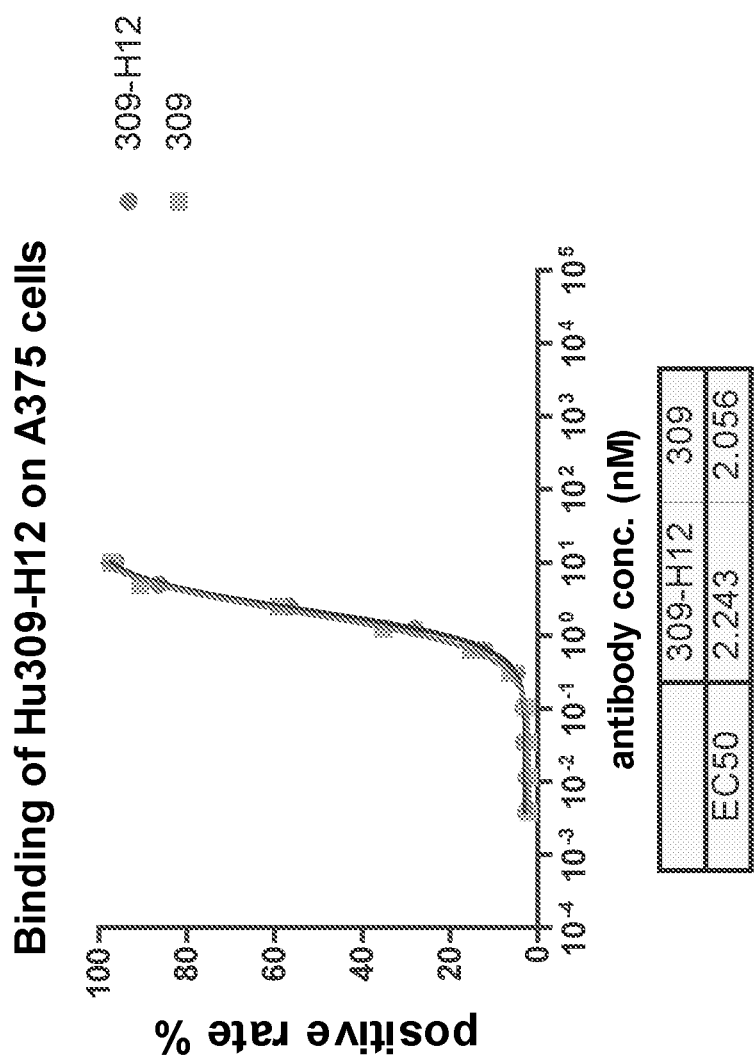
FIG. 4 shows the binding results to cell surface CD73 protein.

As shown in FIG. 4, the bispecific antibody 309-H12 had similar binding activities as hu309 in binding to cell surface CD73.

Figure 5:
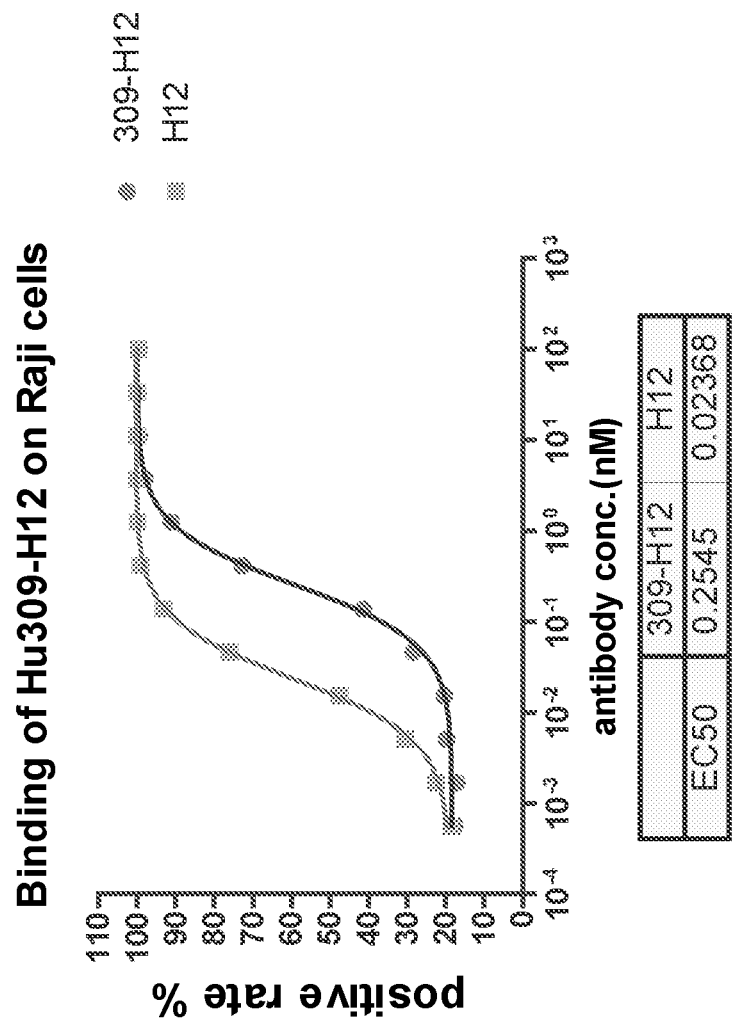
FIG. 5 shows the binding results to cell surface PD-L1 protein.

Using the same procedure, the binding activities of 309-H12 and H12(PDL1) to the human PD-L1 protein from PD-L1 positive Raji cells. Although the binding activities of the bispecific antibody was lower than the monospecific one, both of the activities were high (FIG. 5).

Example 4. Blocking of CD73 Activity by the Bispecific Antibody

This example shows that the 309-H12 antibody was as effective as the monospecific hu309 antibody in blocking CD73 enzymatic activities.

A sample containing 400 pM (0.0252 µg/ml) CD73 was used. Antibodies were diluted from 4 nM (hu309 0.6 µg/ml, 309-H12 0.8 µg/ml) by 2 fold. CD73 and each antibody were pre-incubated for 30 min at 37° C., and AMP (100 µM) and ATP (100 µM) and incubated for 6 hrs at 37° C. Equal volumes of cell titerglo was then added to the samples.

Figure 6:
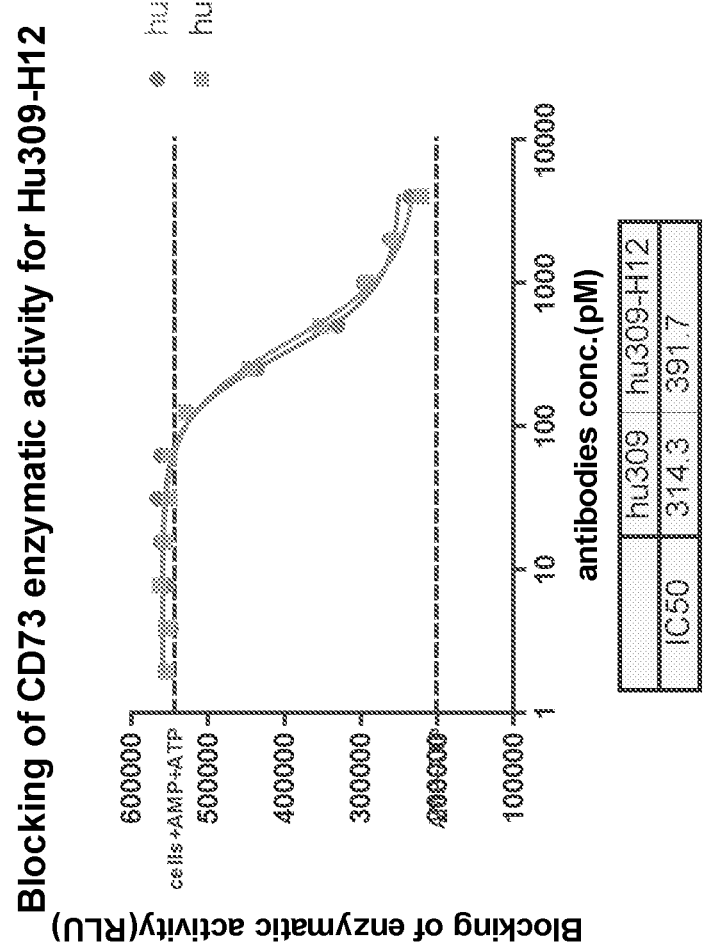
FIG. 6 shows that the bispecific antibody blocked soluble CD73 enzymatic activity.

As shown in FIG. 6, the bispecific antibody 309-H12 had similar ability as hu309 in blocking the enzymatic activity of soluble CD73.

Figure 7:
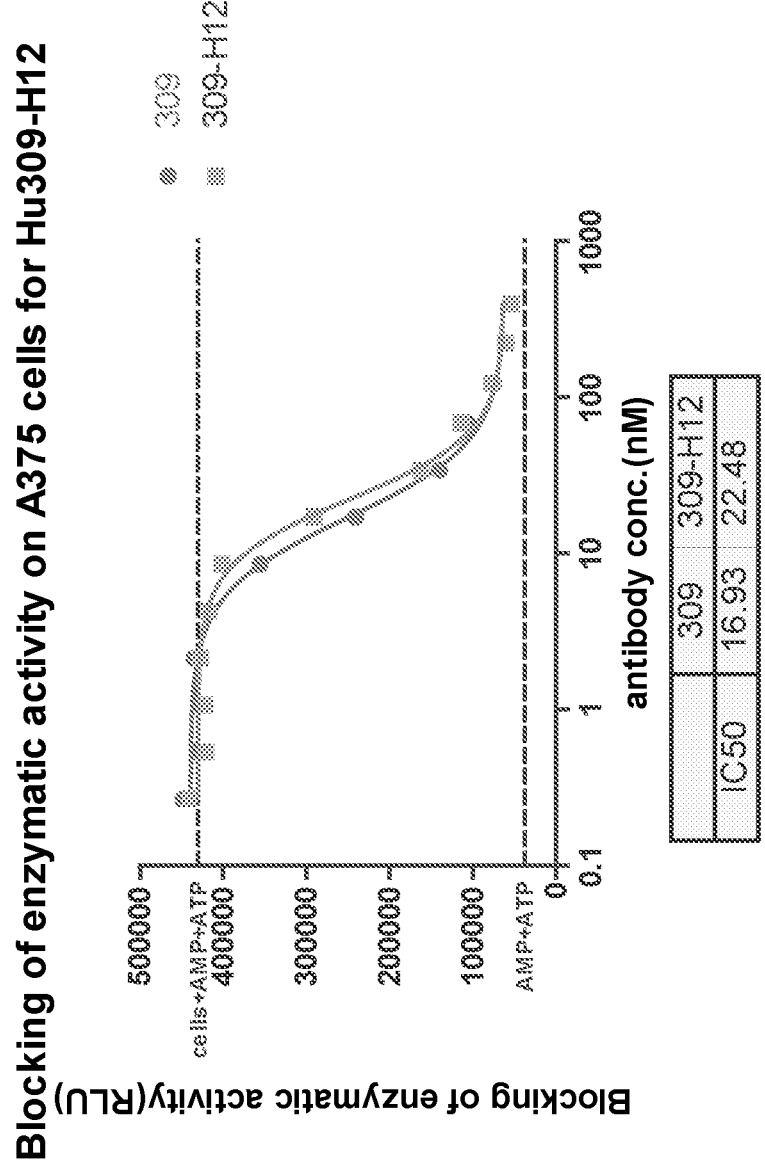
FIG. 7 shows that the bispecific antibody blocked cell surface CD73 enzymatic activity.

Similar results were obtained for these antibodies in blocking cell surface CD73 enzymatic activity (FIG. 7). The A375 cells were used in this test. The samples contained 50 µl of 15000 A375 cells in DMEM, and the antibodies were serial diluted from 160 nM (hu309 240 µg/ml, 309-H12 320 µg/ml), 25 µl per well, 37° C. for 30 min. AMP: 800 µM 25 µl per well, 17-24 hr. After 17-24 hr, 50 µl of cell supernatants were transferred into 96-well black plate, and 50 µl of 40 µM ATP were added. 100 µl of cell titerglo was then added into black plate.

Example 5. T-Cell Activation

This example shows that the 309-H12 bispecific antibody was able to block PD-L1 to PD-1 binding, resulting in TCR activation and increased IL-2 production.

Figure 8:
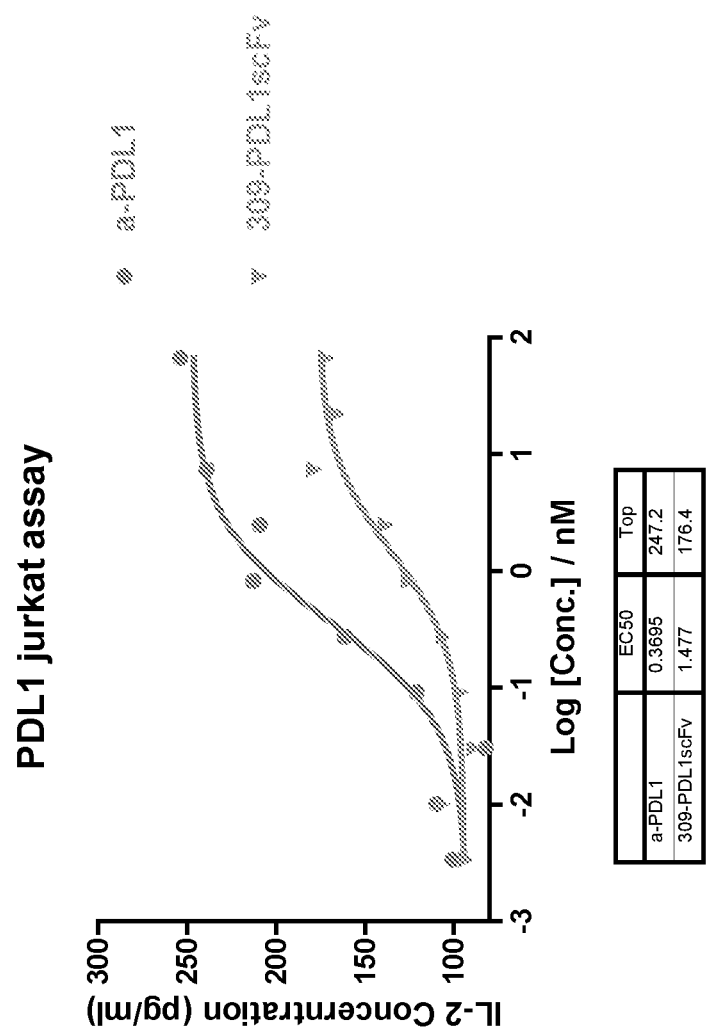
FIG. 8 shows that the bispecific antibody blocked cell surface PD-L1 to PD-L1 binding, resulting in T-cell activation.

PD-1 effector cells which are Jurkat T cells expressing human PD-1 and IL-2 reporter driven by an NFAF response element and PD-L1+ cells which are Raji cells expressing human PD-L1 were used in this assay. The two cell types were co-cultured in the presence of TCR stimulation (SEE superantigen), the PD-1/PD-L1 interaction inhibited TCR signaling and NFAT-mediated IL-2 production. Addition of PD-L1 antibody H12 or the bispecific antibody 309-H12 blocked the PD-1/PD-L1 interaction, thereby releasing the inhibitory signal and resulting in TCR activation and increased IL-2 production (FIG. 8).

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. A bispecific antibody comprising an anti-CD73 portion and an anti-PD-L1 portion,
wherein the anti-CD73 portion has binding specificity to a human CD73 protein and comprises a heavy chain variable region comprising a CDRH1 comprising the amino acid sequence of SEQ ID NO:1, a CDRH2 comprising the amino acid sequence of SEQ ID NO:2, and a CDRH3 comprising the amino acid sequence of SEQ ID NO:3, and a light chain variable region comprising a CDRL1 comprising the amino acid sequence of SEQ ID NO:4, a CDRL2 comprising the amino acid sequence of SEQ ID NO:5, and a CDRL3 comprising the amino acid sequence of SEQ ID NO:6, and
wherein the anti-PD-L1 portion has binding specificity to a human PD-L1 protein and comprises a heavy chain variable region comprising a CDRH1 comprising the amino acid sequence of SEQ ID NO:7, a CDRH2 comprising the amino acid sequence of SEQ ID NO:8, and a CDRH3 comprising the amino acid sequence of SEQ ID NO:9, and a light chain variable region comprising a CDRL1 comprising the amino acid sequence of SEQ ID NO:10, a CDRL2 comprising the amino acid sequence of SEQ ID NO:11, and a CDRL3 comprising the amino acid sequence of SEQ ID NO:12.

2. The bispecific antibody of claim 1, wherein the anti-CD73 portion comprises a Fab fragment.

3. The bispecific antibody of claim 2, wherein the anti-PD-L1 portion comprises a single-chain variable fragment (scFv).

4. The bispecific antibody of claim 1, wherein the anti-CD73 portion comprises a single-chain variable fragment (scFv).

5. The bispecific antibody of claim 4, wherein the anti-PD-L1 portion comprises a Fab fragment.

6. The bispecific antibody of claim 3, comprising a first peptide linker between the Fab and the scFv.

7. The bispecific antibody of claim 6, wherein the first peptide linker comprises SEQ ID NO:13 or SEQ ID NO:14.

8. The bispecific antibody of claim 6, wherein the scFv comprises a second peptide linker between the heavy chain variable region and the light chain variable region.

9. The bispecific antibody of claim 8, wherein the second peptide linker comprises SEQ ID NO:13 or SEQ ID NO:14.

10. The bispecific antibody of claim 1, wherein the anti-CD73 portion and the anti-PD-L1 portion form a heterodimer.

11. The bispecific antibody of claim 10, wherein the anti-CD73 portion comprises a Fab fragment, or a single-chain variable fragment (scFv).

12. The bispecific antibody of claim 10, wherein the anti-PD-L1 portion comprises a Fab fragment, or a single-chain variable fragment (scFv).

13. The bispecific antibody of claim 12, wherein the anti-CD73 and the anti-PD-L1 portions each comprises a Fab fragment.

14. The bispecific antibody of claim 1, further comprising a Fc fragment.

15. The bispecific antibody of claim 1, wherein the heavy chain variable region of the anti-CD73 portion comprises the amino acid sequence of SEQ ID NO:21 and the light chain variable region of the anti-CD73 portion comprises the amino acid sequence of SEQ ID NO:22.

16. The bispecific antibody of claim 1, wherein the heavy chain variable region of the anti-PD-L1 portion comprises the amino acid sequence of SEQ ID NO:23 and the light chain variable region of the anti-PD-L1 portion comprises the amino acid sequence of SEQ ID NO:24.

17. The bispecific antibody of claim 1, comprising two heavy chains each comprising the amino acid sequence of SEQ ID NO:15 and two light chains each comprising the amino acid sequence of SEQ ID NO:16.

18. The bispecific antibody of claim 1, comprising two heavy chains each comprising the amino acid sequence of SEQ ID NO:17 and two light chains each comprising the amino acid sequence of SEQ ID NO:16.

19. The bispecific antibody of claim 1, comprising two heavy chains each comprising the amino acid sequence of SEQ ID NO:18 and two light chains each comprising the amino acid sequence of SEQ ID NO:19.

20. The bispecific antibody of claim 1, comprising two heavy chains each comprising the amino acid sequence of SEQ ID NO:20 and two light chains each comprising the amino acid sequence of SEQ ID NO:19.

21. A method of treating cancer in a patient in need thereof, comprising administering to the patient the antibody of claim 1.

22. The method of claim 21, wherein the cancer is selected from the group consisting of bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer.

23. A method of treating cancer in a patient in need thereof, comprising:
    (a) treating a T cell, in vitro, with the antibody of claim 1; and
    (b) administering the treated T cell to the patient.

* * * * *